United States Patent [19]
Bishay et al.

[11] Patent Number: 5,951,598
[45] Date of Patent: Sep. 14, 1999

[54] ELECTRODE SYSTEM

[75] Inventors: Jon M. Bishay, Woodinville; Kent W. Leyde, Redmond; John F. Harris, Bellevue, all of Wash.

[73] Assignee: Heartstream, Inc., Seattle, Wash.

[21] Appl. No.: 08/782,990

[22] Filed: Jan. 14, 1997

[51] Int. Cl.[6] ........................................... A61N 1/04
[52] U.S. Cl. ..................... 607/142; 607/152; 600/372
[58] Field of Search .................... 607/142, 149, 607/152, 153, 4, 5, 145; 128/639–641, 643, 644

[56] References Cited

U.S. PATENT DOCUMENTS

| | | |
|---|---|---|
| 4,419,998 | 12/1983 | Heath . |
| 4,483,103 | 11/1984 | Bickel . |
| 4,610,254 | 9/1986 | Morgan et al. ......................... 607/142 |
| 4,653,503 | 3/1987 | Heath . |
| 4,681,112 | 7/1987 | Jones et al. ................................. 607/5 |
| 4,852,585 | 8/1989 | Heath . |
| 4,895,169 | 1/1990 | Heath . |
| 4,955,381 | 9/1990 | Way et al. . |
| 4,979,517 | 12/1990 | Grossman et al. . |
| 5,080,099 | 1/1992 | Way et al. . |
| 5,137,458 | 8/1992 | Ungs et al. .................................. 607/5 |
| 5,330,526 | 7/1994 | Fincke et al. . |
| 5,352,315 | 10/1994 | Carrier et al. .......................... 607/152 |
| 5,456,710 | 10/1995 | Gadsby .................................. 607/142 |
| 5,466,244 | 11/1995 | Morgan . |
| 5,571,165 | 11/1996 | Ferrari . |
| 5,785,043 | 7/1998 | Cyrus et al. ............................. 128/712 |

OTHER PUBLICATIONS

Printed internet page www.contourmedical.com/new.html disclosing "Quantum Edge" defibrillators, Dec. 1996.
Specification page for Zoll Medical Corporation product "Stat Padz", Mar. 1995.
Fast–Patch®, Physio–Control Disposable Defibrillation/ECG Electrodes.
Quik–Combo™, Physio–Control Disposable Pacing/Defibrillation/ECG Electrodes with Redi–Pak™.
MediTrace® 1110L, Graphic Controls Corp. Combination Defibrillation and ECG Electrode (packaging).
MediTrace® 1210H, Graphic Controls Corp. Combination Defibrillation, Pacing and ECG Electrode (packaging).
Cummins et al. "Automatic External Defibrillators Used by Emergency Medical Technicians" *JAMA* 257(12): 1605–1610 (1987).
Weaver et al. "Influence of External Defibrillator Electrode Polarity on Cardiac Resuscitation" *PACE* 16:285–290 (1993).

(List continued on next page.)

*Primary Examiner*—Jack W. Lavinder
*Assistant Examiner*—David M. Ruddy
*Attorney, Agent, or Firm*—Cecily Anne Snyder

[57] ABSTRACT

This invention relates to medical electrode systems and, in particular, to a defibrillator electrode system for use with an automatic or semi-automatic external defibrillator (AED). This invention provides a medical electrode system with two electrodes. Each electrode has a flexible substrate with an adhesive surface; a conductor disposed on the substrate; and an electrode disposed on the substrate and electrically connected to the conductor. The electrode pads are each imprinted to show the proper placement of the electrode. Additionally, the medical electrode system may have the electrode pads adhered to a single removable releasing surface. The removable releasing surface may have a fold-line along a center axis between the two electrode pads, or alternatively may have perforations along the center axis. Ideally, the imprinting on each electrode pad can be interpreted by an AED operator without reviewing the imprinting of the other electrode pad.

13 Claims, 2 Drawing Sheets

OTHER PUBLICATIONS

Cummins et al. "Training Lay Persons to Use Automatic External Defibrillators: Success of Initial Training and One–Year Retention of Skills" *Am. J. Emerg. Med.* 7(2):143–149 (1989).

Poole et al. "Low–Energy Impedance–Compensating Biphasic Waveforms Terminate Ventricular Fibrillation at High Rates in Victims of Out–of–Hospital Cardiac Arrest" *J. Cardiovascular Electrophys.* 8(12):1373–1385 (1997).

"Public Access Defibrillator II—Top abstract shows that public can use AED" *Currents in Emergency Cardiac Care, American Heart Assn.* (Summer 1997).

R2 Medical System electrode pads.

Physio Control Quik–Combo™ electrode pads.

Zoll Medical Corporation stat•padz™.

Cardiotronics Multi–Pads™.

Laerdal Medical Heartstart® electrodes.

Quantum™ Edge System electrode pads.

ELECTRODE SYSTEM

BACKGROUND OF THE INVENTION

1. Field of the Invention

This invention relates generally to medical electrode systems and, in particular, to a defibrillator electrode system for use with an automatic or semi-automatic external defibrillator (AED).

2. Description of the Prior Art

One frequent consequence of heart attacks is the development of cardiac arrest associated with heart arrhythmias, such as ventricular fibrillation. This abnormal heart rhythm is caused by an abnormal and very fast electrical activity in the heart. During ventricular fibrillation the heart cannot pump blood effectively. Ventricular fibrillation may be treated by applying an electric shock to the patient's heart through the use of a defibrillator. Defibrillation clears the heart of the abnormal electrical activity and allow the heart's natural pacemaker areas to restore normal function. Because blood is no longer pumping effectively during ventricular fibrillation, the chances of surviving a heart attack decreases with time after the attack. Quick response to a heart attack by administering a defibrillating shock as soon as possible after the onset of ventricular fibrillation is therefore often critically important.

Increasing the number of potential defibrillator operators who are trained on the proper use of an external defibrillator increases the likelihood that a trained defibrillator operator will be available during an emergency and thus could ultimately reduce the defibrillator deployment time. As the number of potential operators increases, however, the frequency with which each operator uses the skills developed during training decreases. Depending upon the amount of time since the defibrillator operator last used a defibrillator, review of electrode placement instructions will likely be required to determine correct placement of the electrode pads since failure to apply the electrode pads correctly can reduce the amount of energy that is applied to the heart and may result in a failure of the defibrillation shock. Such a review, while necessary, delays the speed with which defibrillation can be performed on the patient. With every second that passes, the likelihood of successfully restoring the patient's heart to a normal sinus rhythm decreases. Therefore, every step in the deployment and use of a defibrillator that can be streamlined is critical.

One time saving gain has been the development of electrode pads which eliminate the step of attaching the electrode pads to the cable, and, for the most part, eliminate the need to untangle the cable. An example of such an electrode system is described in U.S. Pat. No. 5,466,244 for "Defibrillator Electrode System" by Morgan. Other electrode pads have also been developed that attempt to decrease the amount of time a defibrillator operator spends deploying the electrode pads.

R2 Medical Systems has developed a multi-function electrode system, R2® PADS™, that features two circular electrode pads. Each electrode pad has its own release liner. One electrode pad, approximately 12.5 cm in diameter, is attached to a blue lead line that is integral with the defibrillator connector. A blue label with white writing on this electrode pad reads:

$$\overset{+}{\underset{\text{APEX}}{\text{LL}}}.$$

The second electrode pad, that is noticeably larger at approximately 17 cm in diameter, is attached to a white lead line which is also integral with the same connector. A white label with blue writing on the electrode pad reads:

$$\underset{\text{POST}}{\overset{-}{\text{RA}}}.$$

A more detailed description of the electrode pad system can be found in U.S. Pat. Nos. 4,483,103, 4,852,858, 4,895,169, 4,419,998 and 4,653,503 (Heath). The size differences, lead line coloration, and markings would not assist a defibrillator operator with the correct placement of the electrode pads in an emergency situation, particularly if the operator had not been recently trained or recently used an AED. It is likely that a defibrillator operator would need to return to the packaging to determine how to properly place the electrode pads, taking up precious additional time.

Physio-Control Corporation has developed yet another approach, the QUIK-COMBO™ electrode system also featuring two electrode pads. Both electrode pads are the same size and attached to black lead lines that are integral with a defibrillator connector. Each electrode pad also has its own separate release liner. The first electrode pad has a first label identifying the electrode pad as a QUIK-COMBO™ electrode with a second label imprinted with a red heart attached to the electrode pad where the lead wire from the connector attaches to the electrode pad. The second electrode pad has a first label with a picture depicting the placement of the electrode pads, showing an image of human torso with one electrode pad with a red heart on the lower left side of a torso, and an image of a second electrode pad with no such marking on the upper right. The second electrode pad also has a second label with no markings covering the area where the lead wire from the connector attaches to the electrode pad. The packaging for the electrode pads shows two alternate placement strategies, but warns that the second placement strategy should not be used with AEDs. Failure to either be familiar with the electrode pad system, or to closely read the packaging could result in an incorrect placement of the electrode pads.

Zoll Medical Corporation has developed the STAT PADZ™ multi-function electrode system again featuring two electrode pads. The Zoll electrode pads are each attached to lead wires that are integral with the defibrillator connector. Each electrode pad is attached to a sheet of plastic that is adhered to the interior surface of the product's packaging such that when the packaging is correctly opened along its three seams, the pads will lie exposed on what had been the interior surface of the packaging. When the packaging is sealed after manufacturing for shipping, the upper surfaces of each electrode pad are in contact until the packaging is finally opened. The lower (adhesive) surface of the electrode pads, are, as described above, attached to the plastic liner, which in turn is securely adhered to the interior surface of the product's packaging. The electrode pads are oriented on the interior surface of the packaging so that one lead line is oriented toward the top opening of the packaging while the other lead line is oriented toward the sealed bottom of the packaging. This orientation of the electrode pads results in top-to-bottom orientation of the electrodes and the labeling (described below) once the packaging is opened.

The Zoll first electrode pad is round with two labels. The first label identifies the electrode pad as a "Zoll STAT PADZ". The second label on the first electrode pad depicts the front of a human torso with a round electrode on the lower left side of the ribs. Additionally, the wording on the label indicates "FRONT (Apex) PACE/DEFIB". The second electrode pad is square and also features two labels. Again, the first label on the second electrode pad identifies the electrode pad as a "Zoll STAT PADZ". The second label on the second electrode pad depicts of the back of a human torso with a square electrode on the left side of the spine covering a portion of the shoulder. Additionally the label includes the wording "BACK PACE/DEFIB". The packaging pictures a front torso and a rear torso with the electrode pads positioned thereon.

Cardiotronics has taken another approach with their MULTI-PADS™ electrode pad product. The Cardiotronics electrode pads are the same size, and each is attached to a lead wire that is integral with a defibrillator connector. One electrode pad is labeled "RA" and the second electrode is labeled "APEX". A picture on the packaging shows the correct placement of the "RA" and "APEX" electrode pads. A more detailed explanation of the Cardiotronics electrode pads is found in U.S. Pat. No. 5,080,099 (Way et al.).

U.S. Pat. No. 5,330,526 (Fincke et al.) describes a combined defibrillation and pacing electrode that features a round electrode pad for placement on the chest area of a patient's thorax, and a second rectangular electrode pad for alignment with the spine on the back are of the patient's thorax. According to Fincke et al., the shapes allow for easy placement of the electrode pads in their respective sites on the patient's thorax.

What is needed is a quick and easy to use electrode system which clearly shows the defibrillator operator how to correctly place the electrode pads on a patient without requiring a review of the packaging. What is also needed is a way of marking the electrode pads so that the correct placement of each electrode pad is clear without requiring review of the second electrode pad or requiring extensive familiarity with the particular electrode brand. Ideally, what is needed is an electrode system that will enable an AED operator to deploy and the electrode pads correctly in a minimum amount of time, regardless of how often the operator is called upon to use his or her AED training.

SUMMARY OF THE INVENTION

This invention provides a medical electrode system comprising two electrode pads. Each electrode pad has a flexible substrate with an adhesive surface; a conductor disposed on the substrate; and an electrode disposed on the substrate and electrically connected to the conductor. The electrode pads are each imprinted to show the proper placement of the electrode pads. Additionally, the medical electrode system may have the electrode pads adhered to a single removable releasing surface. The removable releasing surface may have a fold-line along a center axis between the two electrode pads, or alternatively may have perforations along the center axis allowing the releasing surface to be folded. Ideally, the imprinting on each electrode pad can be interpreted by an AED operator without reviewing the imprinting of the companion electrode pad.

Alternatively, this invention provides a medical electrode system comprising first and second electrode pads, each of the first and second electrode pads further comprise a first surface adapted to be placed on a patient and a second surface adapted to be visible when the first surface is placed on a patient. The second surface of the first electrode pad comprises an image of at least a portion of a human body and an image of the first electrode pad on the image of at least a portion of a human body, the second surface of the second electrode pad comprises an image of at least a portion of a human body and an image of the second electrode pad on the image of at least a portion of a human body. Alternatively, the second surface of the first electrode pad may comprise an image of the second electrode pad on the image of at least a portion of the human body. In another alternative, the second surface of the first electrode pad may further comprise an image of an arrow adjacent the image of the first electrode pad. Additionally, the second surface of the second electrode pad may further comprise an image of an arrow adjacent the image of the second electrode.

DESCRIPTION OF THE PREFERRED EMBODIMENTS

Figure 1:
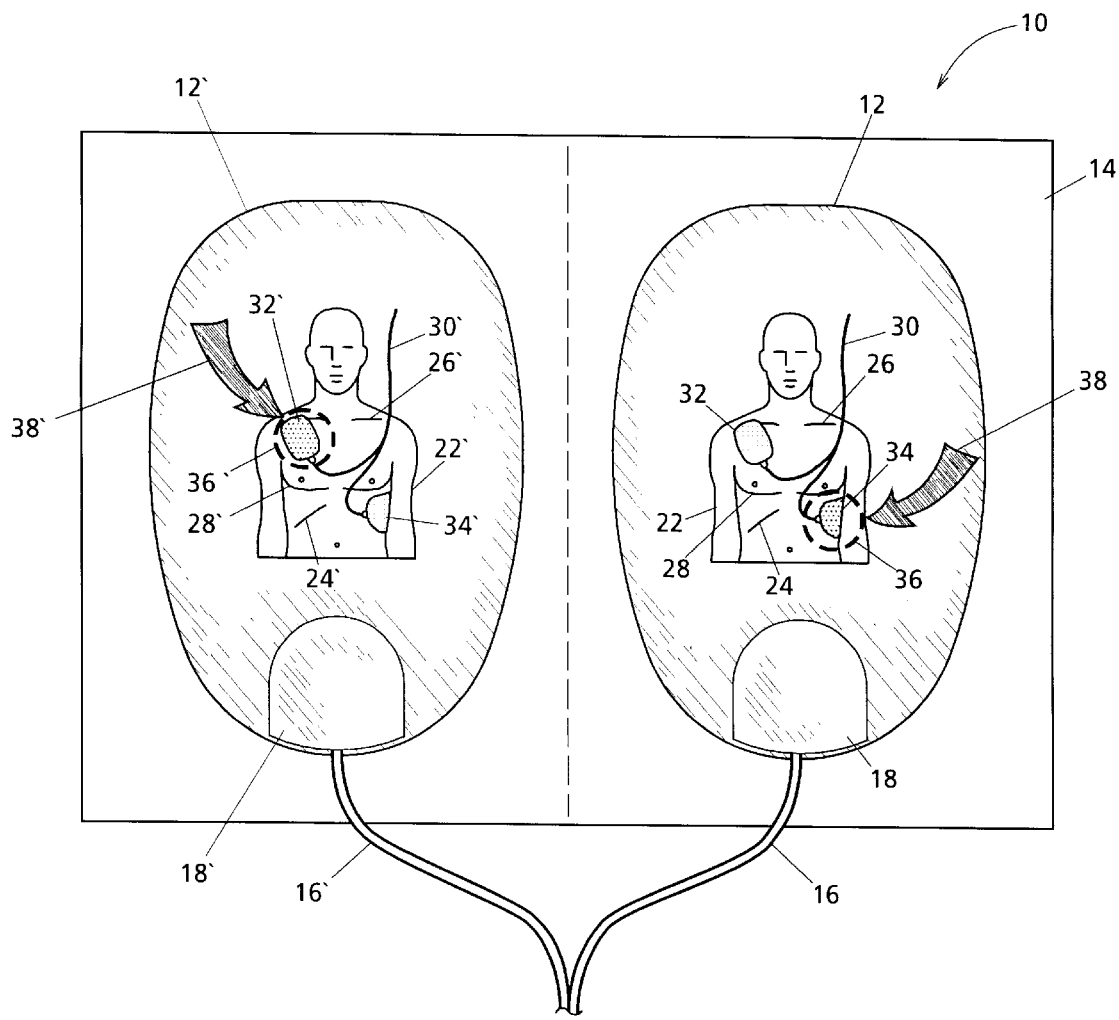
FIG. 1 is a top elevational view of the electrode system according to a preferred embodiment of this invention.

FIG. 1. shows an electrode system according to a preferred embodiment of this invention. As shown in FIG. 1, the electrode system 10 has a pair of electrode pads 12, 12' attached to a releasing surface 14 on opposing sides of a fold or perforated line 20. In this embodiment, the releasing surface 14 is typically manufactured from a non-stick liner. Suitable liners include, for example, a silicone coated polypropylene impregnated release liner. In the embodiment depicted in FIG. 1, the electrodes pads 12, 12' are oriented on the releasing surface 14 so that the lead lines 16, 16' pass from the releasing surface 14 on the same side (in this case the bottom).

Figure 2:
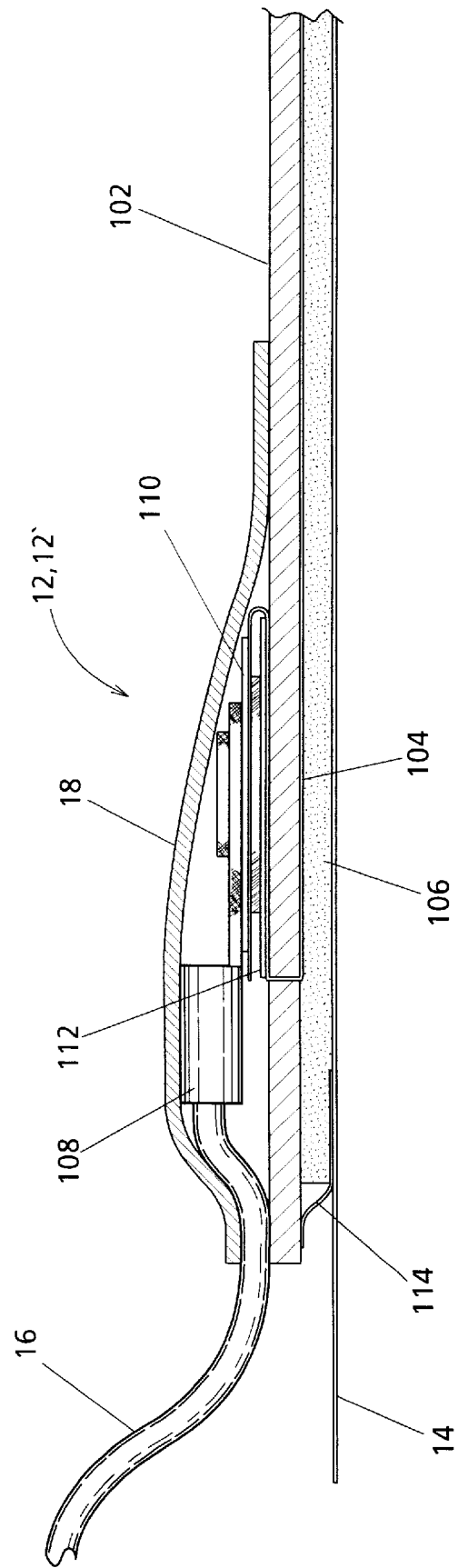
FIG. 2 is a cross-sectional side view of an electrode.

FIG. 2 shows a cross-sectional side view of one of the electrode pads. In this embodiment, the electrode pads 12, 12', are formed of a flexible foam backing 102, each have an electrode disk 104, such as a piece of metal foil, attached to the lower surface of the flexible foam backing 102 with medical grade adhesive. Suitable metal foil would be, for example, 2 mil Tin. The electrode disks 104 are electrically connected to a lead wire 16 between the foam backing layer 102 and the electrode disk 104 on the upper surface of the electrode disk 104. The lower surface of the electrode disk 104 is covered with a layer of conductive gel 106. A suitable conductive gel 106 would be, for example, an RG 63T hydrogel. Additionally, the lead wire 16 may be attached to a ring terminal 108 prior to attaching to the electrode disk 104. Further a washer 110 may be provided between the ring terminal 108 and the electrode disk 104 to improve the electrical connection. Finally an insulating disk 112 may be provided between the electrode disk 104 and the washer 110.

An additional piece of flexible foam 18, 18' may be further provided at the location where the electrical connection 16, 16' attaches to electrode pad.

The conductive gel layer 106 of the electrode pad 12 attached to the silicone coated side of the releasing surface 14. Additionally, a piece of separating tape 114 may be provided to ensure the easy removal of the electrode pad 12 from the releasing surface 14 without damaging the lead wire assembly.

Referring back to FIG. 1, each electrode further comprises an image of at least a portion of a human body 22, 22', typically the human torso. This image may also include, for example, a depiction of the head and face. The image of the human body 22, 22' including the head and face may, for example, be viewed as an anatomical diagram (or 2 dimensional depiction) as shown in FIG. 1. Alternatively, the image of the human body 22, 22' may be a rendered view (or 3 dimensional depiction) of the human torso.

By printing the imaging directly on the electrode pad 12, 12' the maximum conformability of the flexible foam backing 102 is maintained. Maximizing the conformability of the foam backing 102 is desirable because it results in the electrode pad 12, 12' forming a better connection with the patient's skin.

The image of the human body 22, 22' may include a depiction of the rib line 24, 24', the clavicle bone (or collar bone) 26, 26', or the definition of the pectoral muscles 28, 28'. In the preferred embodiment shown in FIG. 1, the depictions of each of the rib line 24, 24', the clavicle bone 26, 26' and the pectoral muscle 28, 28' are provided to aid the operator in quickly understanding that he or she should position the electrode pads on the front of the torso of the patient. Additionally, the image of the human body 22, 22' appears as the mirror image of the defibrillator operator, which corresponds to the positioning of the patient when the electrode pads are applied by the operator during treatment.

Where a rendered image of the human body 22, 22' is used, the human torso may provide more anatomical detail. The rendered depiction may also be viewed so that the left axial line of the patient is evident in order to better depict the correct electrode pad placement on the lower left base of the ribs toward the axial line.

A further image on the electrode pads 12, 12' may be provided that shows the lead line image 30, 30' (which corresponds to 16, 16' of the actual electrode pads) from the defibrillator connector attached two electrode pad images 32, 32' 34, 34' (which correspond to 12, 12' of the actual electrode pads). The first electrode pad image 32, 32' may, for example, be depicted as being attached to the right aspect of the clavicle; the second electrode pad image 34, 34' would then be shown attached to the lower left base of the ribs below the breast.

To assist an operator in determining how to properly attach the electrode pads 12, 12', the image may also provide, for example, a circle 36, 36' around the electrode pad image which corresponds to the correct anatomical placement of the electrode pad. the circle 26, 26' may be formed from a solid line or a dashed line. Alternatively, an arrow 38, 38' may be provided that points to correct anatomical placement for that electrode pad. In a preferred embodiment, the image uses a combination of a dashed circle 36, 36' and the arrow 38, 38' as shown in FIG. 1. Additionally, portions of the image may appear in an alternate color, such as red, or may be bolded, to enhance the operator's ability to quickly asses the correct location for the electrode pad. It is contemplated that a combination of color usage and bolding may be employed to enhance the readability of the images.

In an alternative embodiment, the images of the human body 22, 22', rib line 24, 24', clavicle bone 26, 26', pectoral muscles 28, 28', lead line 30, 30', electrode pads 32, 32', 34, 34', circle 36, 36', or arrow 38, 38' described above may applied to a suitable substrate which is then applied to the non-adhesive surface of the electrode pad 12, 12'. Such a suitable substrate would be, for example, a label with a single adhesive side. Other suitable substrates for transferring the images to the electrode pad surfaces would also be appropriate.

As shown in FIG. 1, electrode pad 12 includes the image of a portion of the human body 22, which includes a depiction of the rib line 24, the clavicle bone 26 and definition of the pectoral muscles 28. The electrode lead lines 30 are depicted attached to an electrode pad 32 at the right aspect of the clavicle and another electrode pad 34 at the lower left base of the ribs. A dashed circle 36 appears around the electrode pad 34 located at the lower left base of the ribs. Additionally, a large arrow 38 points to the same electrode pad 34, clearly indicating that electrode pad 12 corresponds to the electrode pad that should be positioned at the lower left base of the ribs.

Also shown in FIG. 1 is electrode pad 12', which includes the image depicting a portion of the human body 22', showing a depiction of the rib line 24', the clavicle bone 26' and definition of the pectoral muscles 28'. The electrode lead lines 30' are depicted attached to an electrode pad 32' at the right aspect of the clavicle and another electrode pad 34' at the lower left base of the ribs. A dashed circle 36' appears around the electrode pad 32' located at the right aspect of the clavicle. Additionally, a large arrow 38' points to the same electrode pad 32', clearly indicating that electrode pad 12' corresponds to the electrode pad that should be positioned at the right aspect of the clavicle.

In the preferred embodiment, the images on the electrode pads 12, 12' are oriented left-to-left and right-to-right. Therefore, when the operator removes the electrode pads from the packaging, the electrode pad 12 on the right side of the releasing liner 14 corresponds to the right side of the patient as the operator faces the patient (which is the patient's left side); the electrode pad 12' on the left side of the releasing liner 14 has an image corresponding to the left side of the patient as the operator faces the patient (which is the patient's right side). It would therefore be possible for an operator to lie the release liner flat on the patient's stomach and quickly see the orientation of the patient to the electrode pads 12, 12'. Additionally, the operator could apply the electrode pads 12, 12' to the patient's chest without, for example, having to apply electrode pad 12 to the upper right aspect of the clavicle (thus taking it from the right hand side of the releasing liner 14, crossing over the patient's torso and applying it to the upper right aspect of the clavicle) or having to apply electrode pad 12' to the lower left base of the ribs.

When the electrode pads 12, 12' are deployed and the operator removes the electrode pads 12, 12' from the packaging, the surface markings on the electrode pads 12, 12' will be visible to the operator once he or she unfolds the release liner 14. The operator can then remove either electrode pad 12, 12' and correctly apply it to the torso of the patient without having to review the second electrode pad, review the packaging, or review other materials that might be located with the defibrillator.

What is claimed:

1. A medical electrode system comprising:
   first and second electrode pads,
   a lead wire electrically connected to each electrode pad,
   each of said first and second electrode pads comprising a
      first surface adapted to be placed on a patient and a second surface adapted to be visible when the first surface is placed on a patient;
      the second surface of the first electrode pad comprising a single image of at least a portion of a human body and an image of the first and second electrode pads on the image of at least a portion of a human body; and
      the second surface of the second electrode pad comprising a single image of at least a portion of a human body and an image of the first and second electrode pads on the image of at least a portion of a human body; and the electrode system further comprising distinguishing printing on the second surface of the first electrode pad and on the second surface of the second electrode pad distinguishing the first electrode pad from the second electrode pad.

2. The medical electrode system of claim 1 wherein the distinguishing printing on the second surface of the second electrode pad further comprises an image of an arrow adjacent the image of the second electrode pad.

3. The medical electrode system of claim 1 wherein the distinguishing printing comprises a circle drawn around an image of an electrode pad.

4. A medical electrode system comprising a first and second electrode pad each having:

a flexible substrate with an adhesive surface; and an electrode disposed on the substrate and electrically connected to a lead wire, wherein each electrode pad is imprinted to show a single image of a portion of a human body and the proper placement of both of the electrode pads; and further comprising distinguishing printing on each electrode pad distinguishing the first electrode pad from the second electrode pad.

5. The medical electrode system of claim 4 wherein the distinguishing printing on each electrode pad comprises an arrow directed to an image of one of the electrode pads.

6. The medical electrode system of claim 4 wherein the distinguishing printing on each electrode pad comprises a circle drawn around an image of one of the electrode pads.

7. The medical electrode system of claim 4 wherein the imprinting on each electrode pad includes an image of an electrode at the right aspect of the clavicle and an image of an electrode at the lower base of the ribs.

8. The medical electrode system of claim 4 wherein the flexible substrate of each of the electrode pads are each adhered to a single removable releasing surface.

9. The medical electrode system of claim 8 wherein the removable releasing surface further comprises a fold-line along a center axis between the two electrode pads.

10. The medical electrode system of claim 8 wherein the removable releasing surface further comprises perforations along a center axis between the two electrode pads.

11. A medical electrode system comprising:

an electrode pad and a lead wire connected to the electrode pad, the electrode pad comprising a first surface adapted to be placed on a patient and a second surface adapted to be visible when the first surface is placed on a patient, the second surface comprising a single image of at least a portion of a human body, images of first and second electrode pads on the image of the human body, and distinguishing printing identifying which of the images of the first and second electrode pads corresponds to the electrode pad.

12. The medical electrode system of claim 11 wherein the distinguishing printing comprises an arrow directed to an image of one of the electrode pads.

13. The medical electrode system of claim 11 wherein the distinguishing printing on each electrode pad comprises a circle drawn around an image of one of the electrode pads.

* * * * *